United States Patent
Boppart et al.

(10) Patent No.: US 10,813,553 B2
(45) Date of Patent: Oct. 27, 2020

(54) HANDHELD OPTICAL PROBE IN COMBINATION WITH A FIXED-FOCUS FAIRING

(75) Inventors: Stephen A. Boppart, Champaign, IL (US); Paul Scott Carney, Champaign, IL (US); Andrew Cittadine, Chicago, IL (US)

(73) Assignee: Diagnostic Photonics, Inc., Chicago, IL (US)

( * ) Notice: Subject to any disclaimer, the term of this patent is extended or adjusted under 35 U.S.C. 154(b) by 0 days.

(21) Appl. No.: 14/001,556

(22) PCT Filed: Mar. 1, 2012

(86) PCT No.: PCT/US2012/027261
§ 371 (c)(1),
(2), (4) Date: Aug. 26, 2013

(87) PCT Pub. No.: WO2012/118958
PCT Pub. Date: Sep. 7, 2012

(65) Prior Publication Data
US 2013/0345558 A1 Dec. 26, 2013

Related U.S. Application Data (60) Provisional application No. 61/448,345, filed on Mar. 2, 2011.

(51) Int. Cl.
*A61B 5/00* (2006.01)
*G01B 9/02* (2006.01)
*G01B 11/00* (2006.01)

(52) U.S. Cl.
CPC .......... *A61B 5/0073* (2013.01); *A61B 5/0066* (2013.01); *A61B 5/0084* (2013.01);
(Continued)

(58) Field of Classification Search
CPC ... A61B 5/0073; A61B 5/0066; A61B 5/0084; A61B 3/102; G01B 11/00; G01B 9/2087;
(Continued)

(56) References Cited

U.S. PATENT DOCUMENTS 5,050,436 A * 9/1991 Kunii ..................... G10K 11/30
73/644
5,163,107 A * 11/1992 Garriss ........................... 385/74
(Continued)

FOREIGN PATENT DOCUMENTS

WO    WO 2006/084279 A2    8/2006

OTHER PUBLICATIONS

European Patent Office, Supplementary European Search Report—Application No. EP 12752521.0-1657, dated Jul. 15, 2014 (7 pages).
(Continued)

*Primary Examiner* — Amanda Lauritzen Moher
(74) *Attorney, Agent, or Firm* — Sunstein LLP (57) ABSTRACT

An intraoperative probe and a system for optically imaging a surgically significant volume of tissue or other scattering medium. An illumination source generates an illuminating beam that is conveyed to the vicinity of the tissue and a beam splitter, that may be no more than an optical phase reference, splits the illuminating beam into a sample beam along a sample beam path and a reference beam along a reference beam path. A scanning mechanism scans a portion of the sample beam across a section of the scattering medium, while a detector detects return beams from both the reference beam path and the sample beam path and generates an interference signal. A processor computationally moves an effective focus of the sample beam without physical variation of focus of the sample beam. The probe may have a sterilizable fairing that may be detachable.

6 Claims, 2 Drawing Sheets

(52) U.S. Cl.
CPC .............. *G01B 9/02* (2013.01); *G01B 9/0203* (2013.01); *G01B 9/0205* (2013.01); *G01B 9/02049* (2013.01); *G01B 9/02054* (2013.01); *G01B 9/02063* (2013.01); *G01B 9/02083* (2013.01); *G01B 9/02087* (2013.01); *G01B 9/02091* (2013.01); *G01B 11/00* (2013.01); *G01B 2290/65* (2013.01)

(58) Field of Classification Search
CPC .. G01B 9/02054; G01B 9/02049; G01B 9/02; G01B 9/02083; G01B 9/0203; G01B 9/0205; G01B 9/02091; G01B 9/02063; G01B 2290/65
See application file for complete search history.

(56) References Cited

U.S. PATENT DOCUMENTS

| | | | | |
|---|---|---|---|---|
| 5,202,558 A * | 4/1993 | Barker | .................... | G01P 3/366 250/227.21 |
| 5,622,170 A * | 4/1997 | Schulz | ................. | A61B 5/0064 356/141.1 |
| 5,847,827 A * | 12/1998 | Fercher | ................. | A61B 3/102 356/493 |
| 6,307,633 B1 | 10/2001 | Mandella et al. | ............ | 356/479 |
| 6,485,413 B1 | 11/2002 | Boppart et al. | ............... | 600/160 |
| 6,685,639 B1 * | 2/2004 | Wang | ....................... | A61N 7/02 600/439 |
| 6,931,170 B2 * | 8/2005 | Yun et al. | ........................ | 385/18 |
| 7,602,501 B2 | 10/2009 | Ralston et al. | ............... | 356/497 |
| 7,643,155 B2 | 1/2010 | Marks et al. | ................. | 356/497 |
| 8,499,635 B2 * | 8/2013 | Klessel et al. | .................. | 73/602 |
| 2002/0183625 A1 * | 12/2002 | Ostrovsky | ........... | A61B 1/0008 600/476 |
| 2003/0004412 A1 * | 1/2003 | Izatt | ..................... | A61B 5/0066 600/425 |
| 2004/0089816 A1 * | 5/2004 | Quake et al. | .............. | 250/458.1 |
| 2005/0254060 A1 * | 11/2005 | Alphonse | ........... | A61B 5/0066 356/479 |
| 2005/0283058 A1 | 12/2005 | Choo-Smith et al. | ........ | 600/315 |
| 2007/0038043 A1 | 2/2007 | Gelikonov et al. | ........... | 600/315 |
| 2007/0066871 A1 * | 3/2007 | Yang | .................. | A61B 1/00096 600/173 |
| 2007/0081166 A1 | 4/2007 | Brown et al. | .................. | 356/479 |
| 2008/0021276 A1 * | 1/2008 | Wax | .................... | 600/122 |
| 2008/0024767 A1 * | 1/2008 | Seitz | .................. | G01N 21/4795 356/73 |
| 2008/0089641 A1 | 4/2008 | Feldchtein | ....................... | 385/26 |
| 2008/0140341 A1 | 6/2008 | Ralston et al. | ............... | 702/155 |
| 2009/0086213 A1 * | 4/2009 | Masuda | ........................ | 356/479 |
| 2009/0086216 A1 | 4/2009 | Marks et al. | ................. | 356/511 |
| 2009/0177094 A1 | 7/2009 | Brown et al. | .................. | 600/476 |
| 2009/0185191 A1 * | 7/2009 | Boppart | ............... | A61B 5/0066 356/479 |
| 2009/0221920 A1 | 9/2009 | Boppart et al. | ............. | 600/476 |
| 2009/0323076 A1 | 12/2009 | Li et al. | ........................ | 356/479 |
| 2010/0157308 A1 | 6/2010 | Xie | ................. | 356/477 |
| 2010/0166293 A1 | 7/2010 | Sugita et al. | ................. | 382/154 |
| 2010/0253949 A1 * | 10/2010 | Adler | ................. | A61B 5/0066 356/479 |
| 2010/0262020 A1 | 10/2010 | Backman et al. | ............ | 600/478 |

OTHER PUBLICATIONS

European Patent Office, Examination Report, Application No. 12 752 521.0, dated Sep. 20, 2019, 6 pages.

* cited by examiner

HANDHELD OPTICAL PROBE IN COMBINATION WITH A FIXED-FOCUS FAIRING

The present Application claims the priority of U.S. Provisional Patent Application Ser. No. 61/448,345, filed Mar. 2, 2011, which is incorporated herein by reference.

TECHNICAL FIELD

The present invention relates to an apparatus and methods for optically imaging a surgically significant volume of tissue by means of a hand-held probe without requiring active focusing.

BACKGROUND ART

Optical coherence tomography (OCT) has proven to be an advantageous modality for noninvasive optical imaging in scattering media such as biological tissue, and is increasingly finding application in clinical diagnosis and research. Its application in surgery and microsurgery is suggested by the high resolution OCT can afford in a compact and readily integrated format. Such a probe is addressed in WO 2006/084279 (University of Florida), for example, which is incorporated herein by reference.

A major limitation attendant to existing OCT probes, however, is that the depth of focus is typically far shorter than the available imaging depth. Imaging is limited to the available confocal volume, which is smaller than the volume physically accessible to the imaging illumination. In order for the entire imaging depth to be available using existing techniques, the distance to focus must be varied relative to the body of the probe, and some focal technique must be implemented, as taught, for example, by Xie, et al., *GRIN lens rod based probe for endoscopic spectral domain optical coherence tomography with fast dynamic focus tracking*, Opt. Express, vol. 14, pp. 3238-46 (2006), which is incorporated herein by reference.

Consequently, a probe that allows for three-dimensional imaging of a volume within the scattering medium without requiring that the focus be mechanically varied over the useful imaging depth would be highly desirable.

SUMMARY OF EMBODIMENTS OF THE INVENTION

In accordance with various embodiments of the present invention, a tomographic imaging system is provided for imaging a volume within a scattering medium. The system has an illumination source for generating an illuminating beam and an optical fiber for conveying the illuminating beam generated by the illumination source to the vicinity of the scattering medium. A beam splitter, which may be no more than a phase reference surface, splits the illuminating beam into a sample beam along a sample beam path and a reference beam along a reference beam path. A transverse scanning mechanism, disposed within an intraoperative probe, is provided for scanning the sample beam across a section of the scattering medium while a reflective element returns the reference beam along the reference beam path. A detector detects return beams from both the reference beam path and the sample beam path and generates an interference signal. Finally, a processor computationally moves an effective focus of the sample beam without physical variation of focus of the sample beam.

In accordance with alternate embodiments of the present invention, the sample path of the tomographic imaging may be characterized by a fixed focal depth into the scattering medium, and the fixed focal depth, in turn, may be determined in part by a fairing covering at least a portion of the intraoperative probe. The intraoperative probe may be handheld by an operator, and may also be adapted for endoscopic or laparoscopic manipulation.

In certain embodiments of the invention, the beam splitter may be disposed within the intraoperative probe. A reflective element may be provided for returning the reference beam along the reference beam path, and it, too, may be disposed within the intraoperative probe.

In accordance with some embodiments of the invention, the sample path and the reference path coincide in part. The optical fiber may be mode-preserving, and the transverse scanning mechanism may be microelectromechanical.

In accordance with other embodiments of the present invention, a fairing may cover a portion of the intraoperative probe. The fairing may be adapted to serve as a sterile barrier between components of the intraoperative probe and the scattering medium. A focusing element may be disposed within the intraoperative probe for focusing the sample beam into the scattering medium, and the fairing may be adapted to provide a fixed offset distance between the focusing element and the scattering medium. The portion of the intraoperative probe covered by the fairing may include the entirety of the hand-held probe.

In further embodiments of the present invention, the fairing may include a distal tip disposed at an end of the hand-held probe proximate the scattering medium, and the distal tip may be substantially transparent to the sample beam and may include a focusing element of the sample beam. The distal tip may be adapted to serve as an optical phase reference for the interferometric tomography system, moreover a reflective element, or a plurality of reflective elements, may be integral with the distal tip of the fairing. An effective reflectivity of the reflective element may be varied by virtue of orientation of the reflective element with respect to a lens disposed within the reference beam path, where the lens may be a graded index lens.

In yet further embodiments of the present invention, the processor may be of a kind generating an extended-region image, more particularly, the processor may be of a kind employing interferometric synthetic aperture microscopy for generating an extended-region image without physical variation of focus of the sample beam. A camera may provide a real-time visual image of a surface of the scattering medium being tomographically imaged.

In accordance with a further aspect of the present invention, an intraoperative probe is provided for imaging a volume within a scattering medium. The intraoperative probe has an optical fiber for receiving an illuminating beam, a transverse scanning mechanism for scanning the sample beam across a section of the scattering medium, and a detachable sterile fairing extending over an end of the hand-held probe proximate the scattering medium, wherein the sterile fairing includes a distal tip which is substantially transparent to the sample beam.

In some, but not all, embodiments of the present invention, the intraoperative probe is hand-held. The intraoperative probe may also have a beam splitter for splitting the illuminating beam into a sample beam along a sample beam path and a reference beam along a reference beam path, as well as a reflective element for returning the reference beam along the reference beam path. A portion of the distal tip may be substantially reflective of the reference beam. In various embodiments, the sample beam path and the reference beam path may coincide in part, up to substantially an entirety of the respective paths. A single optic may serve both to transmit the sample beam and to reflect the reference beam. The transverse scanning mechanism may be microelectromechanical, and the intraoperative probe may also have an intensity adjustment mechanism, or a polarization adjustment mechanism, within the reference beam path. The detachable sterile fairing may enclose the hand-held probe in substantial entirety.

In accordance with a further aspect of the present invention, a disposable fairing is provided for enclosing an intraoperative probe of a tomographic imaging system. The disposable fairing is characterized by substantial transparency to a scanning sample beam transmitted from the intraoperative probe to a volume within an imaged scattering medium. The disposable fairing may have an integral reflector for reflecting a reference beam, as well as a hard distal tip covering an end of the intraoperative probe proximate to the imaged scattering medium. The fairing may include a film jacket covering connecting cables that couple the intraoperative probe to a source of illumination and to a detector.

BRIEF DESCRIPTION OF THE DRAWINGS

The foregoing features of the invention will be more readily understood by reference to the following detailed description, taken with reference to the accompanying drawings, in which.

DETAILED DESCRIPTION OF EMBODIMENTS OF THE INVENTION

Definitions

As used herein and in any appended claims, the term "image," used as a noun or as a verb, and unless otherwise required by context, refers to the creation of a holomorphic mapping of values characterizing points in space such that the values may, thereafter, be associated, one-to-one, with particular points in space. The values may be stored in a memory, or displayed on a monitor, or fixed in a medium. The values mapped in the creation of an image are typically scalar, such as the scalar susceptibility associated with each point in the volume of the imaged sample. However, the mapping of a vector (or tensor) property of the sample, whether in two or three dimensions, and whether also incorporating other dimensions such as frequency or time (or some other experimental value, such as temperature, for that matter), will also be considered "imaging" for purposes of the following description and claims.

The term "interferometric tomography system," as used herein and in any appended claims, shall be comprehensive and shall subsume systems referred to as low-coherence imaging systems, and of optical coherence tomography (OCT), whether time-domain, spectral-domain, or swept-source, and all other interferometric tomography systems currently known or subsequently invented of which the hand-held probe described herein may form a part.

The term "beam splitter," as used herein and in any appended claims, shall include any element, or feature of an element, that serves to split differential between distinct components of a beam. Thus, for example, the beam splitter may include a dedicated component such as a directional coupler or circulator, and may also include the polished end of a fiber which gives rise to a distinguishable reflection of a beam component, along a common path, where that beam component may serve as a reference beam. A device feature, such as the surface of an optic, that provides an optical phase reference serves as a "beam splitter."

The adjective "intraoperative" describes an imaging probe that may be positioned, or repositioned, by an operator, such as a surgeon, based upon an image that is being displayed in real time, or near real time. An intraoperative probe may include a probe that is directly hand-held by a surgeon, pathologist, or other healthcare professional, and, additionally, a probe that is manipulated endoscopically or laparoscopically.

The term "fairing," as used herein and in any appended claims, refers to a cover used to encase a portion, or all, of a hand-held probe, which cover may be transparent, in whole or in part, and may have segments of varying degrees of flexibility and conformance with the surface contour of the underlying probe or portions thereof. A fairing, as defined herein, may also be referred to by other terms.

The term "transverse scanning," or any mechanism associated therewith, is not limited to linear scanning of a beam to positions within a plane but encompasses scanning along any line or surface, including Cartesian, helical, or circular scanning, such as by rotation transverse to the axis of an endoscope, for example.

The expression "in part," as used herein and in any appended claims, shall encompass within its scope both a proper subset of the entirety and also the entirety.

Interferometric synthetic aperture microscopy (ISAM) is one of a class of methods of tomographic optical microscopy. ISAM brings together the power of computed imaging and inverse scattering together with interferometric broadband optical imaging. Solution of an inverse scattering problem entails two steps. In preparation for applying inverse scattering technique, a forward model is derived, as described, for example, in U.S. Pat. No. 7,643,155 (to Marks et al., hereinafter, "Marks '155") based on scattering of light by inhomogeneities in the sample susceptibility. In a second step, a signal based on coherent detection of scattering from the sample is used to infer a three-dimensional susceptibility of the sample based on comparing the detected signal to data predicted from the forward scattering model. Thus, the objective in formulating the forward model is to derive an expression for the data in terms of the unknown object susceptibility. Coherent detection of the scattering signal is performed using a device that interferes the scattering return from the sample against a reference signal derived from the same source as the sample signal. Hand-held probes in accordance with embodiments of the present invention are such devices.

Detailed practice of ISAM principles may be understood with reference to the following articles and patent literature, all of which are incorporated herein by reference:

Ralston et al., "Inverse scattering for optical coherence tomography," *J. Opt. Soc. Am. A*, vol. 23, pp. 1027-37 (2006).

Ralston et al., "Inverse scattering for high-resolution interferometric microscopy," *Opt. Lett.*, vol. 31, pp. 3585-87 (2006).

Ralston et al., "Interferometric synthetic aperture microscopy," *Nat. Phys.*, vol. 5, pp. 129-34, (2007).

Marks et al., "Inverse scattering for frequency-scanned full-field optical coherence tomography," *J. Opt. Soc. Am. A*, vol. 24, pp. 1034-41 (2007), hereinafter, "Marks (2007)".

Ralston et al., U.S. Pat. No. 7,602,501 (Oct. 13, 2009).

Marks et al., U.S. Pat. No. 7,643,155 (Jan. 5, 2010).

As taught by Marks (2007), wide-field OCT is an interferometric technique, so the phase as well as the amplitude is measured. To bring an image into focus, it is simply necessary to appropriately rephase the field. Marks (2007) derived and demonstrated a method of performing inverse scattering in full-field OCT to reconstruct images of out-of-focus planes, which obviates the need to scan the focus through the volume. The solution of the inverse scattering problem implies that, neglecting vignetting and aberrations, the achievable resolution is space invariant and is the same away from the focus plane as at the focal plane.

By means of the methods described in U.S. Pat. No. 7,602,501, computed imaging techniques are employed to reconstruct features that are both inside and outside the focus. Instead of scanning the focus through the sample, the focus is fixed at the surface of the sample (or in another plane, as described in col. 11, lines 14ff of U.S. Pat. No. 7,602,501), and no relative translation is needed between the objective and the sample. A frequency-swept source can be utilized to provide a new degree of freedom, replacing information lost by fixing the focus, without sacrificing detail outside of the focus. Because the objective and sample can remain fixed relative to each other, no translation hardware is needed which makes placing the objective on a fiber optic or a handheld probe easier.

Regardless of the type of detection used, the beam orientation is fixed while the axis is translated over the sample on a Cartesian grid in directions orthogonal to the beam axis and subsequent axial scans are displayed on adjacent lines to form a tomogram. Suppose the beam is generated by light emerging from an optical fiber and then propagating through a lens to form a focused beam incident on the sample. With the axis of the fiber passing through the point $r_0$ in the Z=0 plane and with the waist plane of the focused field at $z=z_0$, the incident field may be described by the power spectrum $|A(k)|^2$ and a normalized mode g such that $$U_i(r,r_0,k)=A(k)g(r-r_0). \quad (1)$$

The beam may be described in a plane wave decomposition, $$g(r-r_0,k)=1/(2\pi)^2 \int d^2q e^{iq\cdot(r-r_0)} e^{ik_z(q)(z-z_0)} \tilde{g}_0(q,k), \quad (2)$$

where $\tilde{g}_0$ is the two dimensional Fourier transform of g in the $z=z_0$ lane, and the dispersion relation is given by $k_z = \sqrt{k^2-q^2}$. The beam waist is assumed to depend on the wave number, as $W_0(k)=\alpha/k$ where $\alpha=\pi/NA$ and NA is the numerical aperture of the output lens. Thus $$\tilde{g}_0(q,k)=e^{-q^2 W_0^2/2}=e^{-q^2\alpha^2/(2k^2)}). \quad (3)$$

The scattered field, within the first Born approximation, is given by $$U_S(r,r_0,k)=\int d^3 r' G(r',r,k) U_i(r',r_0,k)\eta(r'). \quad (4)$$

Making use of the expressions above for the incident field, $$U_S(r,r_0,k)=A(k)\int d^3 r' G(r',r,k) g(r'-r_0,k)\eta(r'). \quad (5)$$

The signal coupled back in to the fiber is given by the projection of the backscattered field onto the fiber mode g at the exit plane of the fiber. Thus $$S(r_0,k)=\int_{z=0} d^2 r U(r,r_0,k) g(r-r_0,k), \quad (6)$$

which becomes $$S(r_0,k)=A(k)\int_{z=0} d^2 r \int d^3 r' G(r',r,k) g(r'-r_0,k) g(r-r_0,k)\eta(r'). \quad (7)$$

The Green function for free-space is given by the angular spectrum $$G(r',r,k)=i/2\pi \int d^2 q e^{iq\cdot(r-r')} e^{-ik_z(q)(z-z')}/k_z(q), \quad (8)$$

where it is assumed that the scatterers are all located such that $z<z'$ for the whole support of the scatterers. Making use of this expression and Eq. (7), it may be seen that the two-dimensional Fourier transform of S with respect to $r_0$ is given by the expression $$\tilde{S}(Q,k)=i2\pi A(k)\int d^2 q \int dz' 1/k_z(q) e^{ik_z(q)(z'-z_0)}$$
$$e^{ik_z(q-Q)(z'-z_0)} e^{-\alpha^2 q^2/2k^2} e^{-\alpha^2|q-Q|^2/2k^2} \tilde{\eta}(Q,z'). \quad (9)$$

This equation may be solved for $\eta$ by blunt numerical methods. Such methods are numerically expensive. An analytic result may be obtained by considering the shifted form of the integral $$\tilde{S}(Q,k)=i2\pi A(k)\int d^2 q \int dz' 1/k_z(q) e^{ik_z(q)(z'-z_0)} e^{ik_z(q-Q)(z'-z_0)}$$
$$e^{-\alpha^2 Q^2/4k^2} e^{-\alpha^2|q-Q/2|^2/k^2} \tilde{\eta}(Q,z'). \quad (10)$$

For large values of $\alpha$ this integral may be evaluated asymptotically. The integrand, modulo the Gaussian, may be expanded in a Taylor series around the point $q=Q/2$, $$e^{i[k_z(q)+k_z(q-Q/2)](z_0')}/k_z(q)=e^{2ik_z(Q/2)(z'-z_0)}/k_z(Q/2)+q\cdot\nabla_q$$
$$e^{i[k_z(q)+k_z(q-Q/2)](z_0-z')}/k_z(q)|_{q=Q/2}+ \quad (10)$$

Replacing this part of the integrand, the leading term is given by an integral over the constant term in the Taylor expansion:

$$\tilde{S}(Q,k)=i2\pi A(k) e^{-\alpha^2 Q^2/4k^2} \int dz' e^{2ik_z(Q/2)(z'-z_0)}/k_z(Q/2)$$
$$\int d^2 q e^{-\alpha^2|q-Q/2|^2/k^2} \tilde{\eta}(Q,z'). \quad (11)$$

The Gaussian integral may be easily carried out and the remaining integral is seen to be a Fourier transform with respect to $z'$, $$\tilde{S}(Q,k)=k^2/\alpha^2 i2\pi^2 A(k) e^{-2ik_z(Q/2)z_0}/k_z(Q/2) e^{-\alpha^2 Q^2/4k^2}$$
$$\tilde{\tilde{\eta}}[Q,-2k_z(Q/2)], \quad (12)$$

where $\tilde{\tilde{\eta}}$ is the three-dimensional Fourier transform of $\eta$. The next term in the expansion yields a contribution proportional to $\alpha^{-4}$. In the extreme limit that NA→1, it may be seen that $\alpha \to \pi$ so that we expect the leading term approximation to be sufficient even in the case of high numerical aperture. It might be noted that this expansion is distinct from the paraxial approximation (essentially a small $|q|$ expansion of $k_z(q)$) which fails as NA→1.

Figure 1:
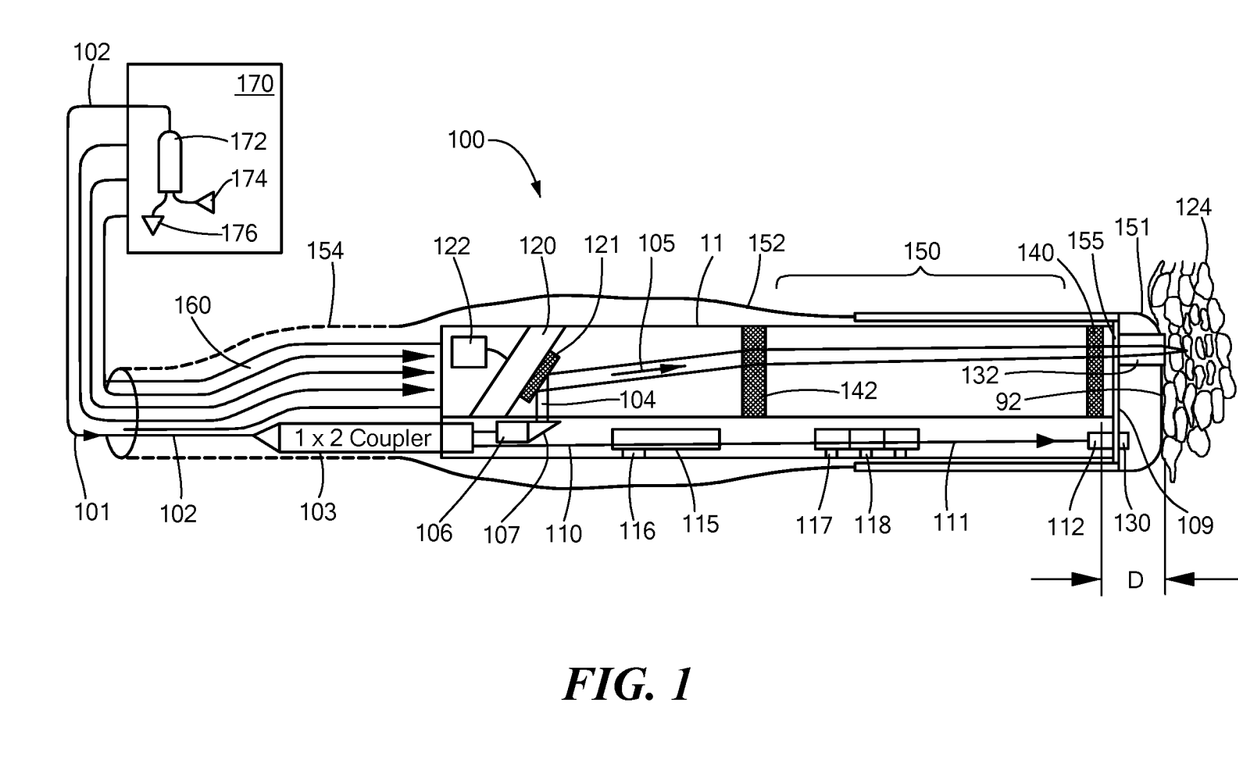
FIG. 1 depicts an intraoperative imaging probe, in accordance with an embodiment of the present invention.

Eq. (12) expresses a resampling scheme illustrated in FIG. 1. To find an appropriate regularization scheme, we will write $$\tilde{S}(Q,k)=\int d\beta H(Q,k,\beta) \tilde{\tilde{\eta}}(Q,\beta), \quad (13)$$

where $$H(Q,k,\beta)=k^2/\alpha^2 i2\pi^2 A(k) e^{-2ik_z(Q/2)z_0}/k_z(Q/2) e^{-\alpha^2 Q^2/4k^2}\delta$$
$$[\beta+2k_z(Q/2)]\equiv f(Q,k,\alpha)\delta[\beta+2k_z(Q/2)]. \quad (14)$$

Then the kernel of the normal operator is given by the expression $$H^*H(Q,\beta,\beta')=|f(Q,1/2\sqrt{\beta^2+Q^2},\beta)|^2\beta/2\sqrt{\beta^2+Q^2}\delta(\beta-\beta'). \quad (15)$$

And the kernel of the Tikhonov regularized psuedo-inverse, with white noise N is given by the expression $$H^+(Q,k;\beta)=\tilde{f}^*(Q,k,\beta)\delta(k-1/2 \sqrt{\beta^2+Q^2})/|\tilde{f}(Q,k,\beta)|^2+2Nk/k_z(Q/2). \quad (16)$$

The object structure is then given by $$\tilde{\eta}^+(Q,\beta)=[\tilde{f}^*(Q,k,\beta)\tilde{S}(Q,k)/|\tilde{f}(Q,k,\beta)|^2+2Nk/k_z(Q/2)]$$
$$k=1/2\sqrt{\beta^2+Q^2} \quad (17)$$

The object structure in the coordinate domain is obtained by applying the three-dimensional inverse Fourier transform.

In accordance with preferred embodiments of the present invention, an intraoperative probe, designated generally by numeral 100, is provided, and is now described with reference to FIG. 1. For heuristic convenience, descriptions are provided herein in terms of a hand-held probe, although it is to be understood that endoscopically and laparoscopically manipulable probes are similarly within the scope of the invention presently described and claimed. Embodiments of the present invention allow the physical focus of the tomographic imaging system to be maintained within a single "plane" disposed within sample 124 while imaging information is derived for the entirety of a sample volume by application of ISAM or any other software approach that reconstructs the three-dimensional susceptibility of the sample. It is to be understood that, within the scope of the present invention, the "plane" of focus may, in fact, refer to a curved two-dimensional surface that departs, to some degree, from geometrical planarity.

An interferometric tomography system, in accordance with embodiments of the present invention, employs the following basic components:

a source of illumination 174, provided by a source of incoherent, or partially coherent, light, and conveyed to the hand-held probe 100 as an illumination beam 101 by a coherence-preserving optical fiber 102, typically a single-mode fiber;

a beam splitter 103 for splitting the illumination beam 101 propagating through optical fiber 102 into a sample beam path 104 and a reference beam path 110. The function of beam splitter 103 is fulfilled, for example, by means of a fiber optical directional 1×2 coupler, although any beam splitter known, or invented in the future, is within the scope of the present invention as described or claimed herein. By way of another example, a 2×2 fiber optical coupler may be employed, as further discussed below. Beam splitter 103 is preferably mode—(and thus also polarization-) preserving. The beam propagating along sample beam path 104 may be referred to herein as a sample beam 105, while the beam propagating along reference beam path 110 (which is preferably an optical fiber) may be referred to as reference beam 111. Additionally, the sample beam path may be referred to herein as the "sample arm," and, mutatis mutandis, the reference path and "reference arm" are the same.

a transverse scanning mechanism, designated generally by numeral 120, that sweeps sample beam 105 across an areal section 92 of sample 124. Sample 124 may be biological tissue, typically in situ. Transverse scanning mechanism 120 is discussed below. Sample beam 105 is attenuated and scattered as it propagates into sample 124.

a reflector 130 that reflects reference beam 111 back to beam splitter 103 for recombination, and interference, at a detector (not shown), with the scatter from sample 124.

In embodiments of the invention in accordance with FIG. 1, the source of illumination and the detector are both disposed in a remote unit 170 distinct from the hand-held probe, which may be referred to as the interferometric tomography engine, or, in the case where the interferometric tomography system employs ISAM, the remote unit may be referred to as the "ISAM engine" 170. In accordance with the embodiment of FIG. 1, an additional directional coupler 172 is provided within the remote unit 170, coupling the source of illumination 174 and the detector 176, respectively, to coherence-preserving optical fiber 102. In alternate embodiments of the invention, there may be a single 2×2 directional coupler in the hand-held unit 110, in which case there are two fibers 102 running from the probe 110 back to the ISAM engine, not just the one shown in FIG. 1. In yet another embodiment of the invention, hand-held probe 110 may contain a 2×2 directional coupler as well as the detector. It is preferred, however, in the case where a spectral-domain ISAM system is employed, that a spectrometer and detector array be disposed remotely from the probe as part of the ISAM engine.

As used herein, incoherence, or partial coherence, as applied to the source of illumination 174, refers to the fact that the electromagnetic field associated with different parts of the emitting surface of the source produce mutually incoherent electromagnetic fields, and do not interfere when averaged over a pertinent time scale such as the inverse bandwidth of the detection system. An example of a spatially incoherent source is the filament of an incandescent light bulb. The spatially incoherent source may be a source of visible or near-infrared light.

In embodiments implementing full-field imaging, the rigorous treatment of which was developed in Marks (2007), the source of illumination of the interferometric imaging system is preferably a spatially incoherent, quasimonochromatic source. In scanned embodiments, on the other hand, typically employing single-mode fiber (SMF), light illuminating the sample is typically spatially coherent. The source of illumination 174 may be characterized by a tunable temporal frequency (or, equivalently, wavelength). In accordance with various methods of employing the hand-held probe taught herein for interferometric imaging, the source may be of a fixed and narrow wavelength band, or may be a broadband source or a swept source. Data may be acquired by any of the foregoing interferometric modalities, with the intensity of interferograms on the detector recorded and processed. From these interferograms, the susceptibility of the sample is inferred.

It should be understood that, in accordance with alternate embodiments of the present invention, sample beam 105 and reference beam 111 may share a common path, and may share the same, or orthogonal, polarization. In one common-path embodiment of the invention, beamsplitter 103 is "degenerate" in that sample beam 105 and reference beam 111 are not physically separated. In that case, a surface of a focusing element 140 or of fairing tip 151, to be discussed below, may serve as reflector 130 while, at the same time, transmitting sample beam 105 into the sample. Reference beam 111 need not be present within hand-held probe 100 at all, within the scope of the present invention, in which case sample beam 105 alone is coupled via optical fiber 102 to the probe.

Referring further to FIG. 1 for other details of embodiments of the present invention, sample beam 105 may be coupled out of directional coupler 103 by means of an optic such as graduated index (GRIN) lens 106. Transverse scanning mechanism 120 may be a microelectromechanical (MEMS)—driven reflector 121 with attendant MEMS-driving electronics 122. Alternatively, sample beam 105 may be scanned electro-optically, or by any other scanning mechanism known in the art or subsequently invented. Transfer optics, such as right angle prism 107—shown by way of example, and focusing elements 140 and 142 may be employed for conveying sample beam 105 onto sample 124 using any means known in the optical arts. A stand-off volume 155 may be provided between focusing optic 140 and cover surface 109 of the hand-held probe 100, the optical path through which constitutes a portion of the fixed distance between optic 140 and a focal plane (or surface). Stand-off volume 155, also referred to as an "air gap," may, alternatively, also be filled with a liquid, glass or other optically transparent material of specified refractive index, as a matter of design choice. Air gap 155, in combination with the thickness of the transparent window 132 (optionally such window may be a focusing element in which case the focusing properties—i.e. a lens focal distance—would also be included) within probe tip 151, defines the focal distance of the instrument.

Focusing element 140 may serve to form a seal against liquid ingress into probe 100. Optionally, an additional optical element, such as glass window 109, may be inserted between the focusing element 140 and the probe tip 151 to seal the probe from liquid ingress. Preferably such element is sufficiently removed from the tissue surface to avoid reflections in the imaging plane. Such optical element may also be coated with an anti-reflective material or aligned off-parallel to a transparent window 132 to minimize internal reflections.

Transparent window 132 in the probe tip 151 may be positioned such that it is in contact with the tissue. Moreover, the optical element designated by numeral 132 may be a powered optic (i.e., a lens), and, as such, serve to focus sample beam 105 into the sample 124 (or scattering medium). As stated above, the hardened plastic end, distal tip 151, may serve to provide a fixed offset distance D between lens 140 and imaged tissue 124 to ensure proper path length and/or optical properties. This is true also with glass 132 on tissue surface and an "air gap" 155 between focusing element 140 and window 132.

Similarly, within reference path 110, a GRIN lens 112 may be provided to couple reference beam 111 from optical fiber to free space, and, more particularly, to reflector 130. An in-line fiber attenuator 115 may be provided for maintaining detector signals within a desired dynamic range, or to optimize signal to noise.

An outer fairing (which is preferably sterilizable, and disposable after a single use, but which may also be fixed, within the scope of the invention) covers a portion, or all, of the hand-held probe 100, and is designated generally, in FIG. 1, by numeral 150. Fairing 150, in turn, may include a distal tip 151, otherwise referred to as a "cap," typically a hard section adapted to cover surface 109 of hand-held probe 100 proximate to sample 124. Distal tip 151 (also referred to, herein, without limitation, as a hard-plastic end), may, for example, be acrylic or polymethylpentene (PMP, or TPX®) or other functional polymer, and may include integrated optical elements such as a window 132 and one or more mirrors 130 necessary for probe function. The distal tip 151 of fairing 150 is, thus, typically, a cylindrical rigid plastic element with an integral end closure that slides over housing 11 of hand-held probe 100. Housing 11 of hand-held probe 100 is preferably machined metal, such as aluminum, while fairing 150 may advantageously provide sterile covering, and serve as a sterile barrier, when used in the sterile surgical field. The disposable fairing 150 preferably allows control with good tactile feedback of the probe controls.

The hardened plastic end, distal tip 151, may serve to provide a fixed offset distance D between lens 140 and imaged tissue 124 to ensure proper path length and/or optical properties. Distal tip 151 may extend over hand-held probe 100 and may transition to a sheath 152 of plastic film, or elastomer, or other material. Sheath 152 may, in turn, transition to a semi-flexible jacket 154 that encases optical fiber 101 and power and control electrical leads 160 that couple hand-held probe 100 to fairing 150.

The distal tip 151 includes an optically transparent window through which sample beam 105 passes for imaging tissue 124. Transparent window 132, may be glass or plastic, for example, or other transparent material appropriate to the wavelength being employed for imaging. Distal tip 151, may also provide the needed phase reference for common-path Doppler, or ISAM data collection, by virtue of a partial reflection from one of the surfaces of transparent window 132. (A description of a common-path Doppler imaging system to which aspects of the present invention may be advantageously applied is provided by Koch et al., Resonant Doppler Imaging with Common Path OCT, Optical Coherence Tomography and Coherence Techniques IV (Andersen et al., eds.) (SPIE-OSA, 2009), incorporated herein by reference.) One or more small partially-reflective mirrors 130 may be integrated into distal tip 151, serving as an optical phase reference for the interferometric system. Multiple mirrors 130 (shown in FIG. 2) may be integrated into distal tip 151 and may be of various reflectivities and available for selection for different tissue types or to optimize the signal-to-noise of the interferometric imaging system. Mirrors may be selectable by sliding distal tip 151 with respect to metal probe housing 11 along various grooves or détentes, each for a different mirror. Distal tip 151 is preferably characterized by a smooth rounded end that facilitates contact and movement across tissue 124 during imaging.

The rigid plastic distal tip 151 of the probe covering fairing 150 is connected to, and/or transitions to a plastic tube-like sheath 152 and jacket 154 that extend proximally from the probe cover tip 151, typically for several meters. This sterile sheath 154 covers the wires/cables 160 of the hand-held probe 110 to maintain sterility when used in the surgical field. This single-use disposable fairing 150, inclusive of the hardened distal tip 151 and flexible sheath 152 and jacket 154 (which may form a single integral part, or multiple parts) is placed over the probe 110 and wires 160 prior to each surgical procedure.

The fairing 150 may also have integrated irrigation and aspiration channels, with connecting plastic tubing integrated into the sheath and exiting at the proximal end, where the irrigation and aspiration channels may be connected to a room saline/water supply and pump, and to vacuum. A footpedal switch, or a button on the probe cover/unit controls irrigation/aspiration, intended to be used to rinse the end of the probe face, and to clear blood/fluids from the probe 110 and/or the tissue 124 to be imaged.

Figures 2, 3:
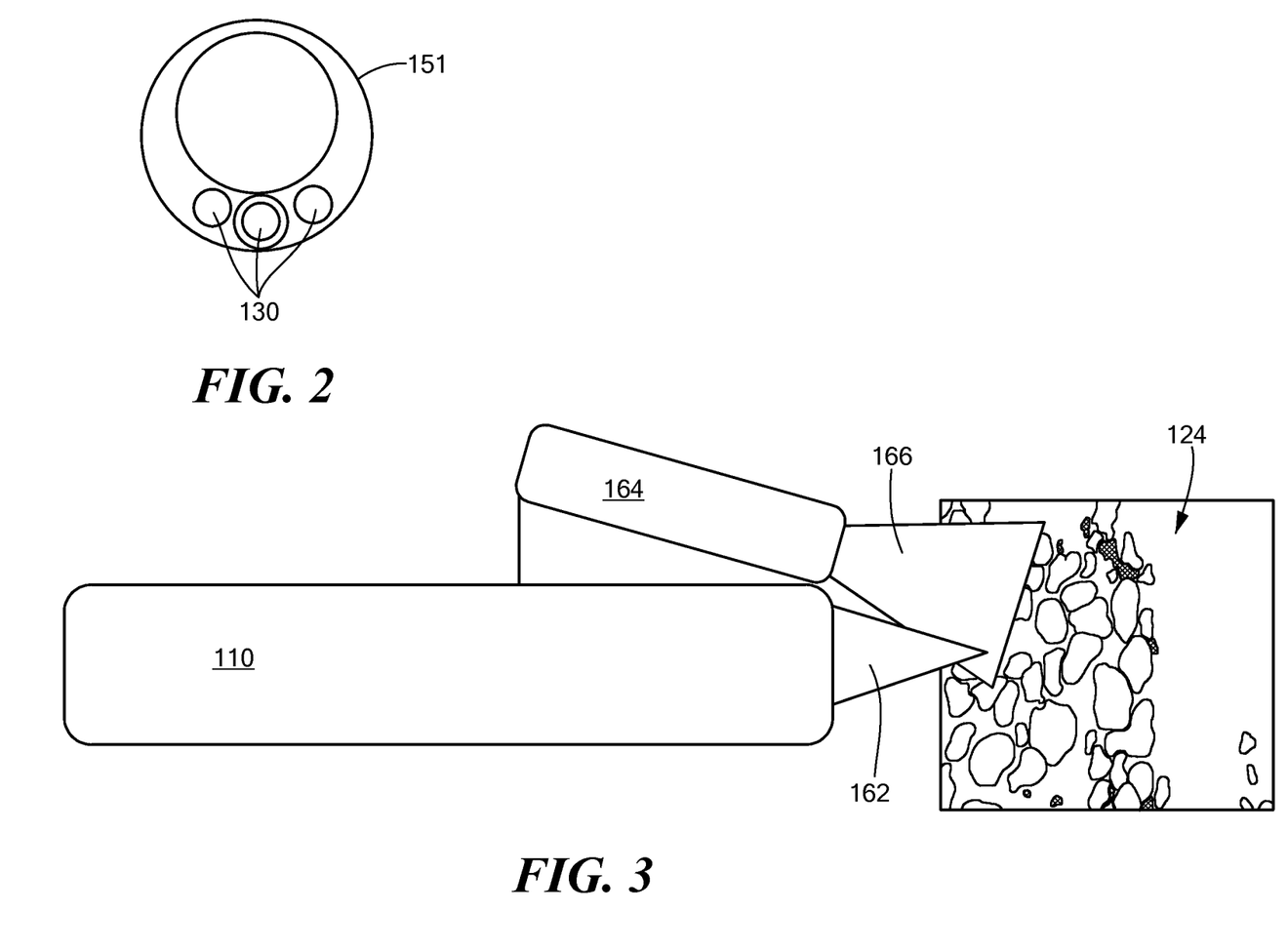
FIG. 2 is a cross sectional view of a fairing tip with multiple mirrors providing selectable reflectivity for the reference beam, in accordance with an embodiment of the present invention
FIG. 3 is a cross-sectional view of an embodiment of the present invention in which an optical camera is attached to a hand-held intraoperative imaging probe.

As now described with reference to FIG. 3, a clip-on video camera 164 may be attached to the hand-held probe 110 to provide a CCD-based real-time video image of the surface of the tissue 124, the volume of which is being imaged using the interferometric tomography system 110, using ISAM, or otherwise. Thus, the surgeon, or other operator, may advantageously visualize the location of the scanning ISAM beam 162, relative to tissue structures. The cylindrical-shaped CCD camera unit 164, when attached to the probe 110, is either angled slightly, such that its field of view 166 allows visualization of the scanned tissue region 124, or uses mirrors to view the tissue surface while keeping the camera unit closer to the probe.

Buttons 115, 117 within the rigid end 151 of the probe fairing 150, may provide for electrical or capacitive control, whether by means of wires running back and integrated with the long sheath or via pass-through buttons that when pressed, contact respective buttons on the probe unit to activate functions such as irrigation/aspiration, CCD video capture, ISAM scan modes, image acquisition/storage, etc.

Housing 11 of hand-held probe 100 is preferably constructed from machined aluminum or hard plastic, and integrates the optical elements and 2-axis MEMS mirror for near common-path interferometry. Various possible beam splitter configurations are discussed above. The reference path fiber passes through an in-line fiber attenuator 115 and can be adjusted manually via set-screw adjustments 116 on the exterior of the probe. The reference fiber then passes through a fiber-based polarization controller 117 with similar set-screw adjustments 118. The reference fiber ends with a GRIN lens 112 to collimate light to be reflected off the variable reflectivity mirrors 130 in the probe cover.

The sample-arm fiber from the coupler is attached to a GRIN lens 106 with right-angle prism 107 to collimate and direct light on to the mirror mounted on the 2-axis MEMS scanner 120. The MEMS scanner 120 directs this light through a series of lens elements 140, 142 to focus the light through the distal tip and probe cover 150 and into the tissue 124. The 2-axis MEMS scanner 120 permits arbitrary scan patterns on the tissue, but the scan patterns are preferably linear/rectangular for 2-D ISAM imaging, square for 3-D ISAM imaging, and cross-shaped, for alignment purposes prior to 3-D imaging.

This distal end of hand-held probe 110 has an optically transparent front face 109 to allow the sample beam 105 and the reference arm beam 111 to pass through with limited attenuation and dispersion.

Controls for operating functions of probe can either be integrated in the probe itself, or operated via foot pedal switches or computer console.

Fiber-optic cable 101 and electrical control and power lines 160 for the MEMS scanner 120 pass out the proximal end of the probe 100, and run back to the main unit console (not shown). All of the foregoing interconnections to the main unit console are covered by disposable jacket 154 when the probe is being used.

A surface of probe tip 151 (whether disposable or permanent) may be used as a signal phase reference for image computation. Either back- or front surfaces may serve that purpose, with the back surface reflectively, or anti-reflectively, coated, as appropriate.

Operation of a probe with a fixed focal plane, in accordance with the present invention, and application of software compensation to computationally move the focus, may advantageously provide a more compact probe. Operation near the focus and far from the focus are discussed in detail in the Marks '155 Patent. It is to be understood that the probe 110 described herein may also be implemented in an endoscopic or transendoscopic modality within the scope of the present invention.

The described embodiments of the invention are intended to be merely exemplary and numerous variations and modifications will be apparent to those skilled in the art. All such variations and modifications are intended to be within the scope of the present invention as defined in the appended claims.

Where examples presented herein involve specific combinations of method acts or system elements, it should be understood that those acts and those elements may be combined in other ways to accomplish the same objective of interferometric tomography. Additionally, single device features may fulfill the requirements of separately recited elements of a claim. By way of specific example, the term "reflective element" need not comprise a distinct component within the scope of the present invention, in that the polished end of a fiber, or a generally transmissive optic, may also provide the reflectivity required to serve as a "reflective element."

The embodiments of the invention described herein are intended to be merely exemplary; variations and modifications will be apparent to those skilled in the art. All such variations and modifications are intended to be within the scope of the present invention as defined in any appended claims.

What is claimed is:

1. A tomographic imaging system comprising:
   a detachable fairing comprising a hard distal tip having an optically transparent window configured for contact with a scattering medium;
   an intraoperative interferometric optical probe including a housing and characterized by a longitudinal axis, the intraoperative interferometric optical probe having optics incapable of focal depth variation during operation of the tomographic imaging system;
   a transverse scanner including at least one driven scanning reflector within the housing of the intraoperative interferometric optical probe adapted to scan a sample beam across the optically transparent window and thereby across a section of the scattering medium at a fixed focal depth; and
   a processor configured to create a tomographic image without variation of a focal depth of the intraoperative interferometric optical probe during operation of the tomographic imaging system,
   wherein the detachable fairing is configured to mount on the intraoperative interferometric optical probe so as to provide a fixed offset distance between the optics within the probe and the scattering medium when the optically transparent window of the hard distal tip is placed in contact with the scattering medium to provide the fixed offset distance in a direction parallel to the longitudinal axis of the probe relative to a surface of contact between the optically transparent window and the scattering medium.

2. A tomographic imaging system in accordance with claim 1, wherein the fairing includes an integral reflector for reflecting a reference beam.

3. A tomographic imaging system in accordance with claim 1, the hard distal tip covering an end of the intraoperative interferometric optical probe proximate to the imaged scattering medium, wherein the hard distal tip includes a glass optic.

4. A tomographic imaging system in accordance with claim 1, the hard distal tip covering an end of the intraoperative interferometric optical probe proximate to the imaged scattering medium, wherein the hard distal tip includes a lens.

5. A tomographic imaging system in accordance with claim 1, wherein the processor is adapted to computationally focus an image of a sample without physical variation of focus of a sample beam.

6. A tomographic imaging system in accordance with claim 1, the fairing including a film jacket covering connecting cables that couple the intraoperative interferometric optical probe to a source of illumination and to a detector.

* * * * *